US00PP29932P3

(12) United States Plant Patent
Cain

(10) Patent No.: US PP29,932 P3
(45) Date of Patent: Dec. 4, 2018

(54) SWEET CHERRY TREE NAMED 'IFG CHER-SIX'

(50) Latin Name: *Prunus avium*
Varietal Denomination: IFG Cher-six

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 0 days.

(21) Appl. No.: 15/530,901

(22) Filed: Mar. 21, 2017

(65) Prior Publication Data

US 2018/0279525 P1 Sep. 27, 2018

(51) Int. Cl.
*A01H 5/08* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181
See application file for complete search history.

(56) References Cited

U.S. PATENT DOCUMENTS

PP6,407 P 11/1988 Bradford

*Primary Examiner* — Anne Marie Grunberg

(57) ABSTRACT

This invention is a new and distinct variety of sweet cherry tree denominated 'IFG Cher-six'. The new sweet cherry tree 'IFG Cher-six' is characterized by producing large size blushed fruits having a reniform shape. The 'IFG Cher-six' has medium firm, medium acid fruit with a good eating quality ripening in mid-season. Fruits are moderately tolerant of rain induced cracking. The tree has a medium-low chilling requirement, produces few doubled and spurred fruits and ripens seven to ten days before the 'Rainier' variety.

1 Drawing Sheet

Latin name of the genus and species claimed: *Prunus avium.*

Variety denomination: 'IFG Cher-six'.

BACKGROUND OF THE INVENTION

The new and distinct cherry tree described and claimed herein originated from hand pollinating the 'Tulare' variety (U.S. Plant Pat. No. 6,407) with pollen of an unidentified early blooming sweet cherry. The hybridization was done in May 2001 in a commercial orchard near Delano, Kern County, Calif. The resulting seeds were collected in May 2001 and were stratified, germinated and the resulting 545 seedlings were planted in a field near Delano, Kern County, Calif. in April 2002. The present variety of sweet cherry tree was selected as a single plant in May 2007 and was first asexually propagated in January 2009 by grafting onto *Prunus mahalab* rootstock. These propagules were found to reproduce true-to-type by asexual propagation. All propagation was done near Delano, Kern County Calif.

BRIEF SUMMARY OF THE INVENTION

Sweet cherries have traditionally been grown in climates with long cold winters and cool to moderately warm summers. Such climates provide enough cold winter temperatures to allow normal growth to resume in the spring and summer temperatures that are low enough not to induce production of unmarketable double or spurred fruit, but it limits the seasonality that cherries are available. The sweet cherry breeding program focuses on developing types of cherries that will grow in regions with low winter chilling and high summer temperatures so that the fruit will ripen before fruit in traditional growing regions.

The new sweet cherry tree 'IFG Cher-six' is characterized by producing large size blushed fruits having a reniform shape. The 'IFG Cher-six' has medium firm, medium acid fruit with a good eating quality ripening in early season. Fruits are moderately tolerant of rain induced cracking. The tree has a medium-low chilling requirement, slightly lower than the 'Brooks' (U.S. Plant Pat. No. 6,676); about 400 to 500 chill hours, and lower than the 'Rainier' (non-patented); about 700 chill hours. It produces fewer doubled and spurred fruits as compared to the 'Brooks' and 'Rainier' varieties in high summer temperature regions such as the Southern San Joaquin Valley of California. Fruits of 'IFG Cher-six' have medium long, medium thick stems that remain attached and stay green during storage and shipping.

In comparison to the 'Rainier' variety, which is the major blush variety grown in the USA, the present variety ripens about seven to ten days earlier and about the same as the 'Brooks' variety. In comparison to 'Tulare', its female parent, the present variety has fruits that have yellow flesh and yellow skin covered with a bright red blush over 50 to 80 percent of its surface as opposed to red flesh and skin color of the female parent. Fruits of 'IFG Cher-six' are larger than those of the 'Tulare' variety.

BRIEF DESCRIPTION OF THE DRAWING

The accompanying photographic drawing in FIG. 1 illustrates in full color 'IFG Cher-six'. The photograph was taken outdoors with indirect lighting. The colors are as nearly true as is reasonably possible in a color representation of this type.

An actively growing shoot tip collected at harvest can be seen in the upper portion of the drawing.

Typical mature fruit, fruit in cross section and cleaned and dried fruit pits are displayed in the lower half of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2001 by The Royal Horticultural Society, London, England.

Throughout this specification subjective description values conform to those set forth by the International Board for Plant Genetic Resources (IBPGR) 'Cherry Descriptor List' (*Prunus* spp.) (1985) which was developed with full support from the Commission of the European Communities (CEC) Programme Committee for Plant Disease Resistance Breeding and the Use of Genebanks.

The descriptive matter which follows pertains to 'IFG Cher-six' plants grown in the vicinity of Delano, Kern County, Calif. during 2016, and is believed to apply to plants of the variety grown under similar conditions of soil and climate elsewhere:

Tree:

General:

*Age.*—7 yrs. old.

*Height.*—3.0 M when pruned.

*Width.*—2.6 M when pruned.

*Vigor.*—Moderately vigorous.

*Density of foliage.*—Dense.

*Form.*—Upright.

*Rootstock.*—*Prunus mahalab.*

*Resistance to.*—Insects: Average typical of *Prunus avium* species. Diseases: Average typical of *Prunus avium* species.

*Chilling requirements.*—Medium-low: 350 to 500 hours.

*Graft compatibility.*—Good; produces compatible graft unions with *Prunus avium*, 'Mazzard' seedling (non-patented) and *Prunus mahaleb* seedlings (non-patented).

Trunk:

*Trunk diameter of 7 year old trees, 30 cm above the soil line.*—11.8 cm.

*Lenticel size.*—Small.

*Lenticel dimensions.*—Length: About 0.8 cm. Width: About 0.2 cm.

*Lenticel shape.*—Elliptical shape oriented horizontally.

*Lenticel color.*—Greyed-white: 156A.

*Trunk surface texture.*—Intermediate.

*Outer bark color.*—The following colors were observed: Greyed-purple: N186A and 187A.

Branches:

1-year old wood:

*Vertical top growth length.*—Medium: About 52.2 cm.

*Horizontal growth length.*—Medium: About 51.7 cm.

*Diameter.*—Vertical growth: 1.9 cm. Horizontal growth: 3.0 cm.

*Internode length.*—About 3.3 cm.

*Number of lenticels.*—Few: Approximately 5 lenticels per linear cm.

*Lenticel size.*—Small.

*Lenticel dimensions.*—Length: about 0.1 cm. Width: about 0.1 cm.

*Lenticel shape.*—Round.

*Bark color.*—The following colors were observed: Grey: 201B and Brown: 200D.

2-year old wood:

*Length.*—About 60.4 cm.

*Diameter.*—About 4.2 cm.

*Internode length.*—About 3.3 cm.

*Number of lenticels.*—Few: Approximately 4 lenticels per linear cm.

*Lenticel dimensions.*—Length: about 0.2 cm. Width: about 0.1 cm.

*Lenticel shape.*—Elliptical shape oriented horizontally.

*Bark color.*—Grey: 201A.

Buds:

Vegetative buds:

*Shape.*—Elongated.

*Vegetative bud dimensions.*—Length: about 1.0 cm. Width: about 0.4 cm.

*Vegetative bud burst.*—About Feb. 12, 2016.

Flower buds:

*Flower bud dimensions.*—Length: about 0.8 cm. Width: about 0.6 cm.

*Shape.*—Oval.

*Placement.*—At bud positions mostly 1 to 7 on first year wood.

*Average number of flower buds on first year wood.*—6.

*Number of flower buds per spur on second year wood.*—3.

*Color.*—Greyed-orange: 166A.

*Flower bud burst.*—About Feb. 14, 2016.

Leaves:

Mature leaves:

*Leaf dimensions.*—Length: About 15.4 cm. Width: About 7.0 cm.

*Leaf shape.*—Ovate, symmetric on both sides of central axis.

*Shape of tip.*—Acuminate: narrowly.

*Shape of base.*—Oblique.

*Margin.*—Serrated: regular: rounded.

*Surface texture.*—Smooth.

*Leaf profile.*—Involute.

Upper surface:

*Upper surface pubescence.*—None.

*Upper leaf surface color.*—Yellow-green: 147A.

Lower surface:

*Lower surface pubescence.*—Dense: all over.

*Lower leaf surface color.*—Yellow-green: 147B.

Petiole:

*Petiole dimensions.*—Length: About 4.5 cm. Width: About 0.2 cm.

*Upper surface of petiole color.*—The following colors were observed: Yellow-green: 144A and Greyed-orange: 166A.

*Lower surface of petiole color.*—Yellow-green: 144B.

*Petiole groove.*—Wide.

*Petiole pubescence.*—Medium: only on lower surface.

*Venation.*—Arcuate.

*Vein color.*—Yellow-green: 144B.

Glands:
*Number of glands.*—2.
*Gland dimensions.*—Length: About 3 mm. Width: About 2.3 mm.
*Gland shape.*—Globose.
*Gland location.*—On petiole.
*Gland color.*—Greyed-purple: 187B.
*Leaf stipule.*—Not present.
Flowers:
*Blooming period.*—Mid-season.
*Blooming dates.*—First Bloom: Feb. 22, 2016. Full Bloom: Feb. 29, 2016.
*Number of flowers per cluster.*—2-4. Average — About 3.
*Corolla.*—Composed of unfused petals, somewhat overlapping.
*Corolla diameter.*—2.9 cm.
*Petal number.*—5.
*Petal length.*—About 1.4 cm.
*Petal width.*—About 1.7 cm.
*Margin waviness.*—Weak.
*Division of upper margin.*—Notched.
*Color of petal upper surface.*—White: 155A.
*Color of petal lower surface.*—White: 155A.
*Peduncle.*—Length: About 1.9 cm. Width: About 0.14 cm.
*Peduncle color.*—Yellow-green: 144A.
*Number of sepals.*—5.
*Sepal length.*—About 0.7 cm.
*Sepal width.*—About 0.5 cm.
*Sepal shape.*—Broad ovate.
*Sepal color.*—Upper surface: Yellow-green: 144C. Lower surface: Greyed-orange: 176A.
*Filament.*—Length: About 0.3 to 1.5 cm. Width: About 0.3 mm.
*Filament color.*—White: 155B.
*Anther color.*—Greyed-orange: 163C.
*Pollen color.*—Greyed-yellow: 162A.
*Pollen production.*—Medium.
*Self-compatibility of flowers.*—Self-incompatible.
*Flower compatibility group.*—S1S6.
Fruit:
General:
*Ripening period.*—Mid-season: Approximately: May 4, 2016.
*Use.*—Fresh market.
*Keeping quality.*—Average.
*% titratable acidity.*—About 0.63%.
*Refractometer test.*—Soluble solids: Brix — About 17.6.
*Firmtech II (g/mm).*—About 292.
*Flavor.*—Good, medium acid, well balanced.
*Juice color.*—Greyed-orange: 163A.
*Juice amount.*—Intermediate.
*Eating quality.*—Good.
Stem:
*Stem.*—Length: About 5.2 cm. Width: About 0.2 cm.
*Stem color.*—Yellow-green: 144A.
*Stem cavity.*—Shallow.
*Stem retention during storage.*—Excellent.
*Stem storage quality.*—Excellent.
Berry:
*Uniformity of size.*—Uniform.
*Shape.*—Reniform.
*Fruit weight.*—About 10.5 gm.
*Apical diameter.*—About 26.1 mm.
*Diameter across suture.*—About 2.2 cm.
*Diameter at right angle to suture plane.*—About 2.7 cm.
*Suture.*—None.
*Percent of excessively deep or split sutures.*—About 0%.
*Doubles.*—About 10%.
Skin:
*Thickness.*—Thin.
*Texture.*—Smooth, tender.
*Skin color.*—The following colors were observed: Yellow-orange: 14C, and Red: 45A and Grey-orange: 163D.
*Tendency to tip crack.*—Somewhat susceptible.
*Tendency to stem cavity crack.*—Slightly susceptible.
*Tendency to suture crack.*—Not susceptible.
Flesh:
*Texture.*—Medium firm.
*Color.*—Yellow: 10D.
Stone:
*Shape.*—Ovate.
*Length.*—About 12.3 mm.
*Width at suture.*—About 9.4 mm.
*Width at right angle to suture.*—About 6.7 mm.
*Type.*—Semi-free.
*Surface texture.*—Smooth.
*Stone color when dry.*—Orange-white: 159A.
*Tendency to split.*—None.
*Base.*—Rounded.
*Apex.*—Broadly pointed.
*Ventral edge.*—Somewhat wide suture subtended by 2 ridges converging at the base and apex, suture often protruding slightly beyond the horizontal plane of the base of the stone.
*Dorsal edge.*—Smooth, narrow ridge from base to apex.

What is claimed:

1. A new and distinct variety of sweet cherry tree as herein illustrated and described.

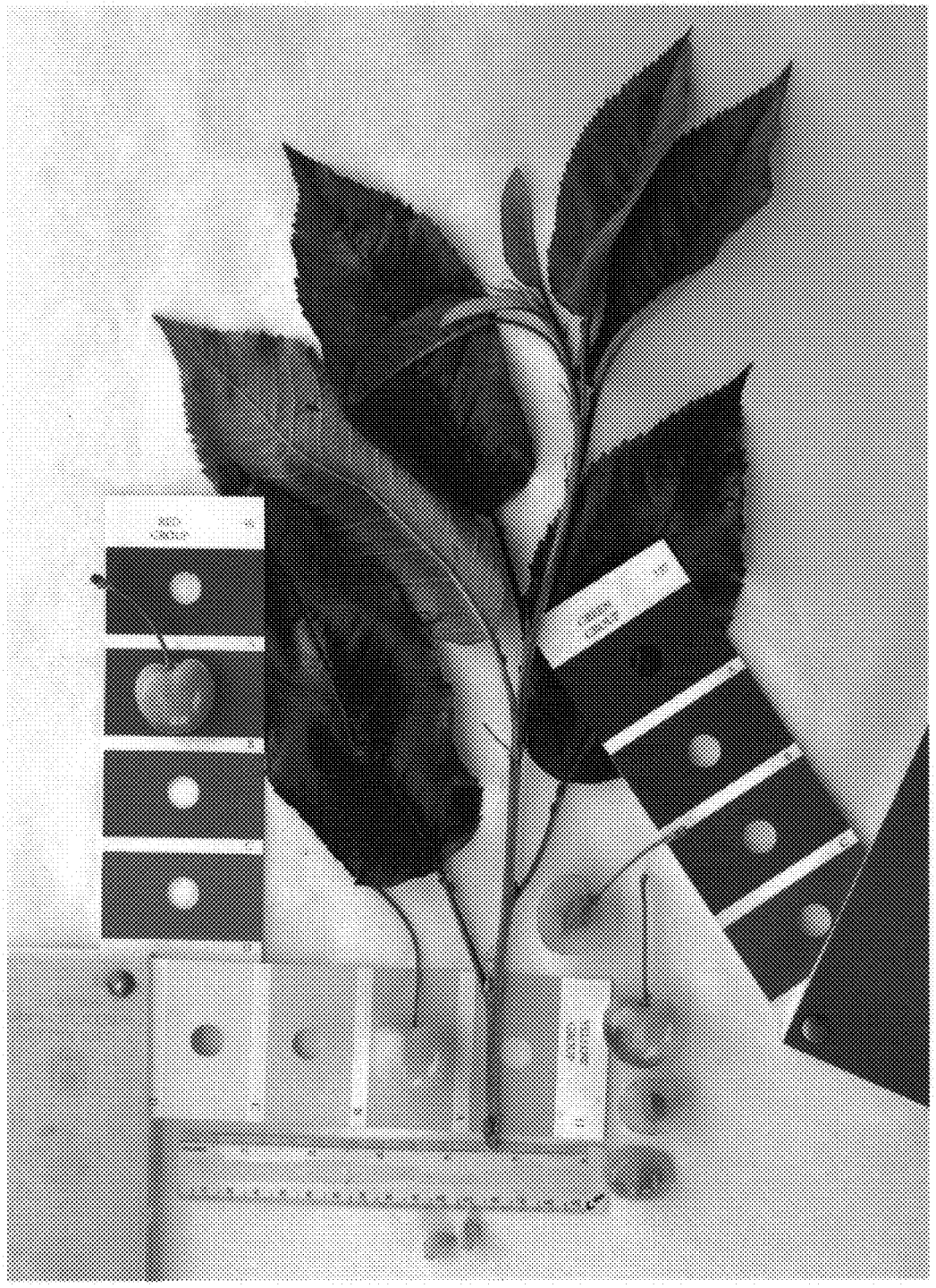

* * * * *